(12) United States Patent
Iqbal (10) Patent No.: US 10,335,400 B2
(45) Date of Patent: Jul. 2, 2019

(54) TREATMENT OF TAUOPATHIES WITH MGLUR5 ANTAGONISTS

(71) Applicant: The Research Foundation for Mental Hygiene, Inc., Menands, NY (US)

(72) Inventor: Khalid Iqbal, Staten Island, NY (US)

(73) Assignee: The Research Foundation for Mental Hygiene, Inc., Menands ( * ) Notice: Subject to any disclaimer, the term of this patent is extended or adjusted under 35 U.S.C. 154(b) by 0 days.

(21) Appl. No.: 14/818,515

(22) Filed: Aug. 5, 2015

(65) Prior Publication Data

US 2016/0038471 A1 Feb. 11, 2016

Related U.S. Application Data

(60) Provisional application No. 62/033,291, filed on Aug. 5, 2014.

(51) Int. Cl.
  *A61K 31/00* (2006.01)
  *A61K 31/44* (2006.01)
  *A61P 25/28* (2006.01)

(52) U.S. Cl.
  CPC .............. *A61K 31/44* (2013.01); *A61P 25/28* (2018.01)

(58) Field of Classification Search
  None
  See application file for complete search history.

(56) References Cited

PUBLICATIONS

Breysse (Chronic But Not Acute Treatment with a Metabotropic Glutamate 5 receptor Antagonist Reverses the Akinetic Deficits in a Rat Model of Parinsonism, The Journal of Neuroscience, Jul. 1, 2002, 22(13):5669-5678).*

Ming-Hong (Blockade of metabotropic glutamate receptors inhibits cognition and neurodegeneration in an MPTP-induced Parkinson's disease rat model, Pharmacology, Biochemistry and Behavior 102 (2012) 64-71).*

Alz.org. Parkinson's Disease Dementia. Electronic Resource: [http://www.alz.org/dementia/parkinsons-disease-symptoms.asp].*

Thibodeau et al. An evolution of the diagnostic criteria for tauopathies. The Canadian Review of Alzheimer's disease and other dementias.*

Muenter et al. Hereditary form of Parkinsonism-dementia. Ann. Neurol. 1998; 43: 768-781.*

Steele. Parkinsonism-dementia complex of Guam. Movement Disorders, vol. 20, Suppl. 12, 2005. pp. S99-S107.*

Arif et al. Tau pathology involves protein phosphatase 2A in Parkinsonism-dementia of Guam. PNAS, Jan. 21, 2014, vol. 111, No. 3, 1144-1149.*

Lobner et al. Beta-N-methylamino-L-alanine enhances neurotoxicity through multiple mechanisms. Neurobiology of Disease, 25, 2007, 360-366.*

* cited by examiner

*Primary Examiner* — Anna Pagonakis
(74) *Attorney, Agent, or Firm* — Bond Schoeneck and King PLLC; David Nocilly; George R. McGuire (57) ABSTRACT

The treatment of abnormal hyperphosphorylation of tau in brains of patients with metabotropic glutamate receptor 5 (mGluR5) antagonists. The treatment uses the signaling pathway in which the inhibition of protein phosphatase 2A (PP2A) through phosphorylation of its catalytic subunit PP2Ac at Tyr$^{307}$ is induced by the activation of metabotropic glutamate receptor 5 (mGluR5) and leads to hyperphosphorylation of tau. The mGluR5-PP2A axis has a central role in neurofibrillary degeneration and thus is be a therapeutic target for the treatment of tauopathies.

4 Claims, 12 Drawing Sheets

TREATMENT OF TAUOPATHIES WITH MGLUR5 ANTAGONISTS

CROSS-REFERENCE TO RELATED APPLICATIONS

The present application claims the benefit of U.S. Provisional Application No. 62/033,291, filed on Aug. 5, 2014.

BACKGROUND OF THE INVENTION

1. Field of the Invention

The present invention relates to the treatment of tauopathies and, more specifically, the use of mGluR5 antagonists for the treatment of tau pathologies.

2. Description of the Related Art

Indigenous residents and immigrants of the Pacific Island of Guam suffer from a high incidence of a progressive and fatal neurodegenerative tauopathy called "parkinsonism-dementia" (PD). This is a long-latency disease with phenotypic characteristics of idiopathic parkinsonism with an early-onset dementia. The disorder is found together with a second high-incidence disease, amyotrophic lateral sclerosis (ALS). The incidence of both diseases has declined dramatically over the past half century, suggesting an environmental etiology. The neuropathology of PD is hallmarked by neurofibrillary tangles (NFTs) of paired helical filaments (PHFs) composed of abnormally hyperphosphorylated forms of the microtubule-associated protein tau. The NFTs found in PD brains are ultra-structurally and biochemically similar to those in Alzheimer's disease (AD).

In contrast to AD pathology, however, studies using postmortem brains confirmed the absence of amyloid β plaques in most PD cases. Many studies have demonstrated that abnormal hyperphosphorylation and aggregation of tau are crucial to neurodegeneration in AD and tauopathies. Although the mechanism leading to the formation of NFTs is still obscure, it has been well recognized that an imbalanced regulation in protein kinases and protein phosphatases can directly cause AD-like tau hyperphosphorylation. Among the various kinases, glycogen synthase kinase-3β (GSK-3β), cyclin-dependent kinase 5, $Ca^{2+}$/calmodulin-dependent protein kinase II (CaMKII), MAP kinase kinase (MEK 1/2), ERK 1/2, protein kinase A, casein kinase 1, and p70 S6 kinase have been most often implicated in tau phosphorylation.

Among the phosphatases, protein phosphatase 2A (PP2A) accounts for ~70% of tau phosphatase activity in the human brain. PP2A is responsible for dephosphorylating most of the hyperphosphorylated sites of tau, and its activity is compromised in the AD brain. Given the increasing evidence that PD histopathologically and genetically should be classified as a tauopathy, identifying the protein kinases/phosphatases and the associated signaling cascades that regulate tau phosphorylation is of crucial importance.

Several etiological factors, especially environmental factors, genetic susceptibility, and metabolic alterations, have been proposed to contribute to PD. The nonprotein amino acid β-N-methylamino-L-alanine (BMAA) has been implicated as a potential environmental factor in PD, ALS, AD, and other neurodegenerative disorders. Although the neurotoxic effects of BMAA are not conclusive, BMAA concentrations as low as 30 µM can cause selective death of motor neurons, and a 10 µM concentration can potentiate neuronal injury induced by exposure to amyloid-β, 1-methyl-4-phenylpyridinium, or methylmercury in mixed cortical cultures. The mechanism of BMAA toxicity is complex and several fold: (i) BMAA displays agonistic properties for NMDA, AMPA/kainate, and metabotropic glutamate receptor 5 (mGluR5) and for mGluR1 receptors in a cell-specific manner, and (ii) it increases intracellular calcium levels and oxidative stress. BMAA was reported to induce learning and memory deficits accompanied by neuronal cell death in rats, although the underlying molecular mechanism by which BMAA affects tau phosphorylation and eventually toxicity has not been established.

BRIEF SUMMARY OF THE INVENTION

The present invention comprises the treatment of abnormal hyperphosphorylation of tau in brains of patients with metabotropic glutamate receptor 5 (mGluR5) antagonists. Parkinsonism-dementia (PD) of Guam is a classical tauopathy in which abnormal hyperphosphorylation of tau leads to neurodegeneration and dementia. The present invention involves the use of signaling pathway in which the inhibition of protein phosphatase 2A (PP2A) through phosphorylation of its catalytic subunit PP2Ac at $Tyr^{307}$ induced by the activation of metabotropic glutamate receptor 5 (mGluR5) leads to hyperphosphorylation of tau. The mGluR5-PP2A axis has a central role in neurofibrillary degeneration in Guam PD and thus may be a therapeutic target for the treatment of this disease and related tauopathies.

More specifically, there is a decrease in protein phosphatase 2A (PP2A) activity associated with an increase in inhibitory phosphorylation of its catalytic subunit PP2Ac at $Tyr^{307}$ and abnormal hyperphosphorylation of tau in brains of patients who had Guam PD. To test the possible involvement of BMAA in the etiopathogenesis of PD, the effect of this environmental neurotoxin on PP2A activity and tau hyperphosphorylation was studied in mouse primary neuronal cultures and metabolically active rat brain slices. BMAA treatment significantly decreased PP2A activity, with a concomitant increase in tau kinase activity resulting in elevated tau hyperphosphorylation at PP2A favorable sites. Moreover, an increase in the phosphorylation of PP2Ac at $Tyr^{307}$ was found in BMAA-treated rat brains.

Pretreatment with metabotropic glutamate receptor 5 (mGluR5) and Src antagonists blocked the BMAA induced inhibition of PP2A and the abnormal hyperphosphorylation of tau, indicating the involvement of an Src-dependent PP2A pathway. Coimmunoprecipitation experiments showed that BMAA treatment dissociated PP2Ac from mGluR5, making it available for phosphorylation at $Tyr^{307}$. These findings suggest that BMAA can lead to tau pathology by inhibiting PP2A through the activation of mGluR5, the consequent release of PP2Ac from the mGluR5-PP2A complex, and its phosphorylation at $Tyr^{307}$ by Src. As a result, metabotropic glutamate receptor 5 (mGluR5) antagonists may be used to treat abnormal tau hyperphosphorylation.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIGS. 2A through 2G are a series of charts and images showing that BMAA inhibits PP2A activity and increases tau hyperphosphorylation in mouse hippocampal primary neurons as follows: (A and B) PP2A activity (A) and PP2Ac protein level (B) were measured in mixed mouse primary hippocampal neurons at 0, 1, 3, 6, and 24 h after treatment with BMAA (1 mM). (C) Representative Western blots showing hyperphosphorylation of tau. (D) Quantification of hyperphosphorylation of tau at different sites and R134d (total tau) shown after normalization with GAPDH. (E and F) Representative photomicrographs (E) and the corresponding quantitation of phospho-tau (12E8) staining (F) in control and BMAA-treated cultured primary neurons. (Scale bar, 100 μm.) (Magnification: 40×.) (G) LDH release was measured 24 h after treatment with BMAA (1 mM) in cultured neurons; 2 mM glutamate was used as a positive control. Data are expressed as mean t SEM for three separate experiments. *P<0.05; **P<0.01.

FIGS. 3A through 3G are a series of charts and images showing that BMAA induces an increase in $pTyr^{307}$ PP2Ac, inhibits the phosphatase activity, and activates several tau protein kinases in rat brain slices. Rat hippocampal brain slices were treated with BMAA (1 mM) for 2 h, and the tissue homogenate was used for Western blots and to measure PP2A activity, as follows: (A) PP2A activity. (B) Western blots. (C) The quantitative analysis of $pTyr^{307}$-PP2Ac, DML309-PP2Ac, $I_1^{PP2A}$, and $I_2^{PP2A}$ of Western blots in B after normalization with total PP2Ac. (D) Western blots of brain slices treated with PP2, an Src kinase inhibitor (10 μM), for 30 min before treatment with BMAA. (E) Quantitative analysis of blots in D. (F and G) The Western blot pattern of total and phosphorylated kinases (F) and quantitation of phosphorylated kinases normalized with the level of corresponding kinase (G). Data are expressed as mean±SEM for three separate experiments. *P<0.05; **P<0.01;

In vitro PP2A activity was measured using purified PP2A holoenzyme in the presence or absence of BMAA. Data are expressed as mean t SEM for three separate experiments. *P<0.05; **P<0.01;

DETAILED DESCRIPTION OF THE INVENTION

Referring now to the drawings, wherein like reference numerals refer to like parts throughout, the present invention is based on the discovery of the involvement of PP2A signaling in PD and a finding that BMAA can produce similar changes by activating the mGluR5 receptor, leading to the dissociation of PP2A from the receptor, followed by its phosphorylation at $Tyr^{307}$ by Src a nonreceptor tyrosine kinase. Phosphorylation of PP2A at $Tyr^{307}$ inhibits its activity and leads to hyperphosphorylation of tau. Together, these finding reveal an etiopathogenic mechanism of neurofibrillary pathology in PD, AD, and ALS involving mGluR5-dependent inactivation of PP2A. The present invention thus seeks to address these taupathies using mGluR5 antagonists. Exemplary mGluR5 antagonists include 2-methyl-6-(phenylethynyl) pyridine, fenobam (1-(3-chlorophenyl)-3-(3-methyl-5-oxo-4H-imidazol-2-yl)urea), CTEP (2-chloro-4-((2,5-dimethyl-1-(4-(trifluoromethoxy)phenyl)-1H-imidazol-4-yl)ethynyl) pyridine) available from F. Hoffmann-La Roche Ltd, mavoglurant (AFQ056) available from Novartis AG, basimglurant (RO4917523) available from F. Hoffmann-La Roche Ltd, and STX107 available from Seaside Therapeutics, Inc. Appropriate dosage may range from 0.1 to 30 mg per kilogram depending on method of administration, which includes oral and subcutaneous administration.

Figure 1A:
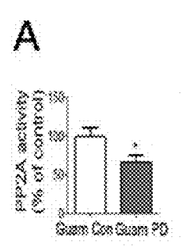
FIGS. 1A through 1E are a series of charts and images showing that PP2A activity is decreased because of the increase in phosphorylation of PP2Ac at $Tyr^{307}$, and tau is hyperphosphorylated in Guam PD brains as follows: (A) PP2A activity assayed by phosphatase ELISA in Guam PD and Guam nonneurological control frontal cortices. (B) Western blots of PP2A and its inhibitors. (C) Quantitative analysis of blots in B. (D) Western blots of tau phosphorylated at different sites. (E) Quantitative analysis of blots in D. Data are expressed as mean t SEM. *P<0.05; P<0.01; *P<0.001.
Figure 1B:
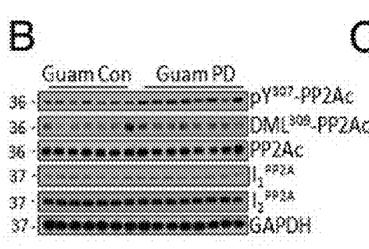
Figure 1C:
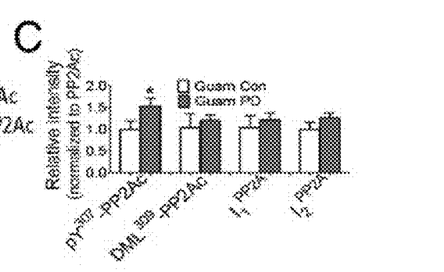
Figures 1D, 1E:
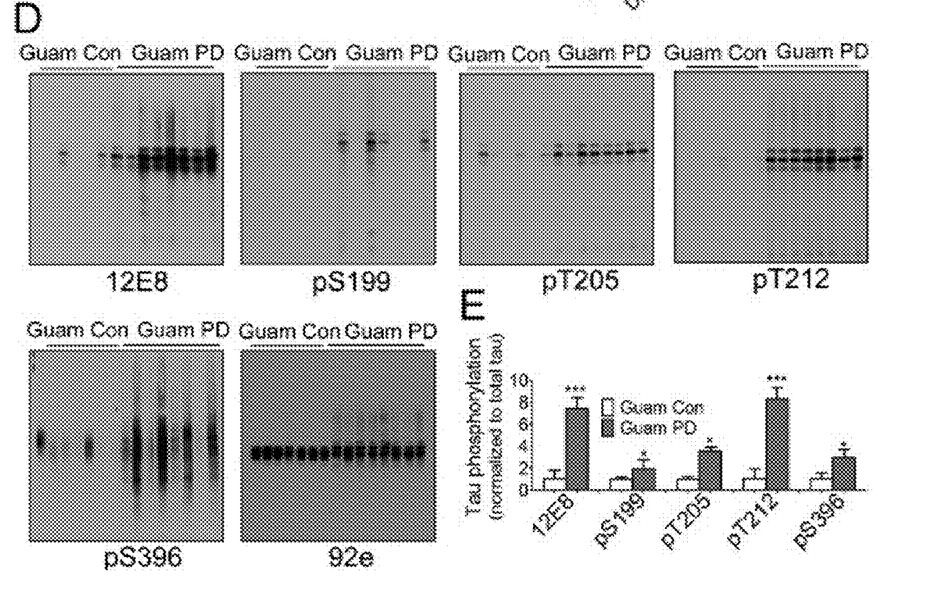

PP2A is the major protein phosphatase that regulates tau phosphorylation in vivo and accounts for 70% of the total tau phosphatase activity in the mammalian brain. In AD brain PP2A activity is compromised, most likely because of the upregulation of its inhibitors $I_1^{PP2A}$ and $I_2^{PP2A}$ and demethylation of its catalytic subunit, PP2Ac. To examine whether PP2A inactivation is involved in abnormal hyperphosphorylation of tau in PD cases, the PP2A activity in autopsied brains from patients with Guam PD and age-matched controls from Guam were assayed by phosphatase ELISA. A significant ($P<0.05$) decrease was found in PP2A activity in PD compared with nonneurological controls from Guam (FIG. 1A). PP2A is known to be down-regulated by phosphorylation at $Tyr^{307}$, demethylation at $Leu^{309}$, and endogenous inhibitors $I_1^{PP2A}$ and $I_2^{PP2A}$. The possible involvement of all PP2A regulatory factors was examined in PD. A significant increase ($P<0.05$) was observed in PP2A phosphorylation at $Tyr^{307}$ in PD brains as detected by quantitative Western blot analysis, as seen in FIGS. 1B and 1C. However, significant changes were not detected in the levels of demethylated PP2Ac or $I_1^{PP2A}$ and $I_2^{PP2A}$ (FIGS. 1B and C). Western blots developed with phosphorylation-dependent/site-specific tau antibodies revealed that tau phosphorylation increased at all phosphorylation sites examined in PD cases as compared with the controls, as seen in FIGS. 1D and 1E.

Similar results were seen in four cases of Guam PD and five age-matched nonneurological control cases from the United States mainland, as seen in FIG. 8. Interestingly, the total tau level was markedly higher in PD cases than in the controls and displayed an upward gel mobility shift with higher molecular weight smears, as seen in FIG. 1D and FIG. 8D, that resemble those previously reported in AD. These data suggest the involvement of $Tyr^{307}$ phosphorylation of PP2Ac in PD brain.

Figure 2A:
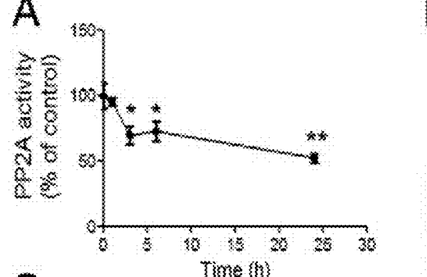
Figure 2B:
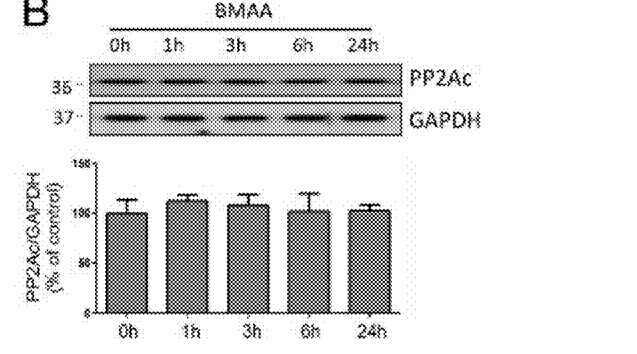
Figure 2C:
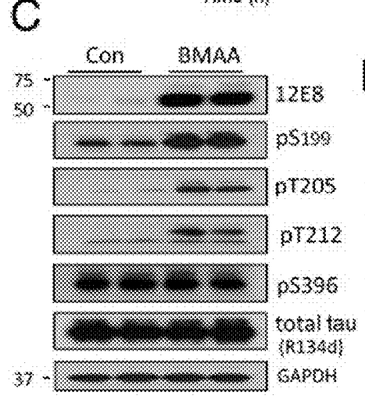
Figure 2D:
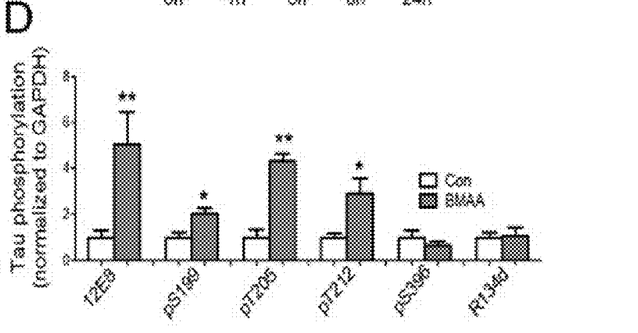
Figure 2E:
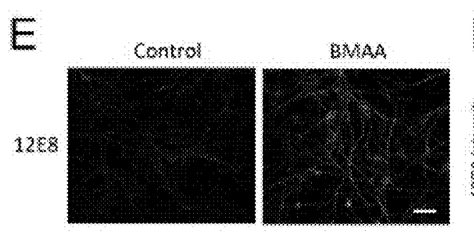
Figure 2F:
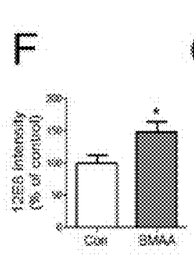
Figure 2G:
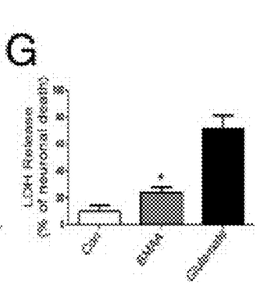

Because BMAA has been widely suspected as a possible environmental toxin in the etiopathogenesis of PD, an investigation was made whether BMAA can inhibit PP2A activity, induce abnormal hyperphosphorylation of tau, and cause neuronal death. The PP2A activity toward phosphorylated tau was determined as a substrate after treatment with BMAA in mouse mixed primary neuronal cultures. BMAA concentrations of 100 µM to 1 mM significantly decreased PP2A activity for 3-48 h without any detectable effect on its protein expression, as seen in FIGS. 2A, 2B and FIG. 9. Quantitative analysis of Western blots developed with site-specific phospho-tau antibodies revealed that hyperphosphorylation of tau was significantly increased at $Ser^{262/356}$ (12E8 site; $P<0.01$), $Ser^{199}$ ($P<0.05$), $Thr^{205}$ ($P<0.01$), and $Thr^{212}$ ($P<0.05$) but not at $Ser^{396}$ in BMAA-treated cells as compared with controls, as seen in FIGS. 2C and 2D. No significant change was found in the level of total tau (R134d) between control and BMAA-treated neurons, as seen in FIG. 2D. Furthermore, immunohistofluorescent analysis revealed that BMAA increased the expression of tau phosphorylated at $Ser^{262/356}$, as seen in FIGS. 2E and 2F. Using a lactate dehydrogenase (LDH) release assay, it was observed that 1 mM BMAA caused cell death in mixed primary neuronal culture, as seen in FIG. 2G, as is consistent with previous reports. Collectively, these results suggest that BMAA can cause cell death which is associated with the inhibition of PP2A and the increase in hyperphosphorylation of tau in primary neurons.

Figure 3A:
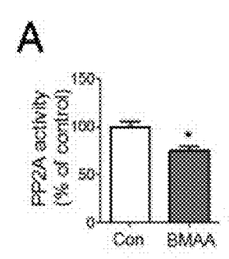
Figure 3B:
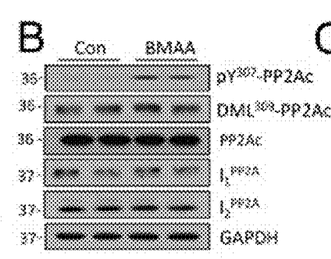
Figure 3C:
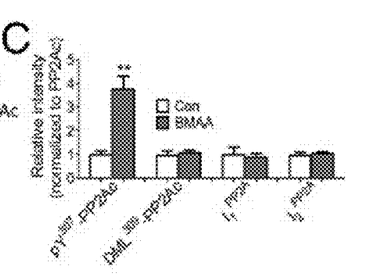
Figure 10A:
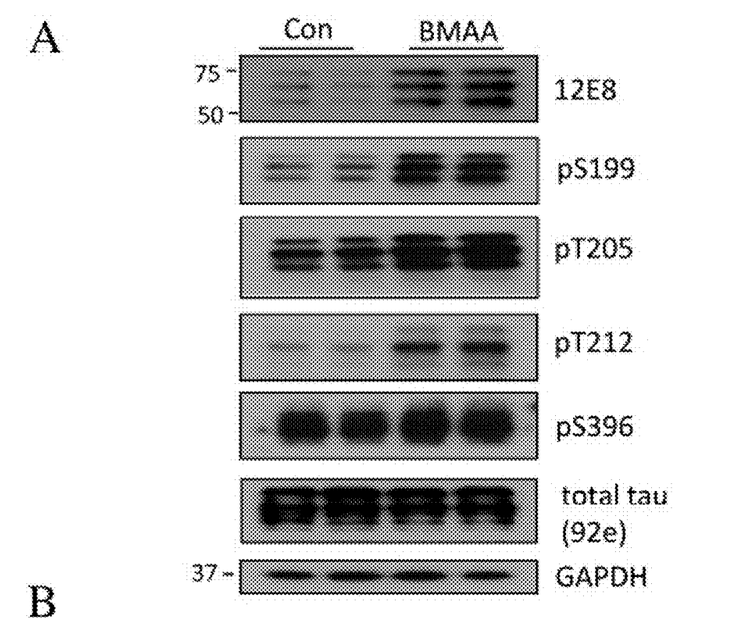
FIGS. 10A and 10B are images showing BMAA induces tau hyperphosphorylation in metabolically active rat brain slices. Rat brain slices were treated with BMAA (1 mM) for 2 h, and the tissue homogenate was used for Western blots to detect the level of tau hyperphosphorylation at different sites. (B) Quantitative analysis of blots in A after normalization with total tau (92e); GAPDH was used as an internal loading control. Data are expressed as mean±SEM for two separate experiments. *P<0.05.
Figure 10B:
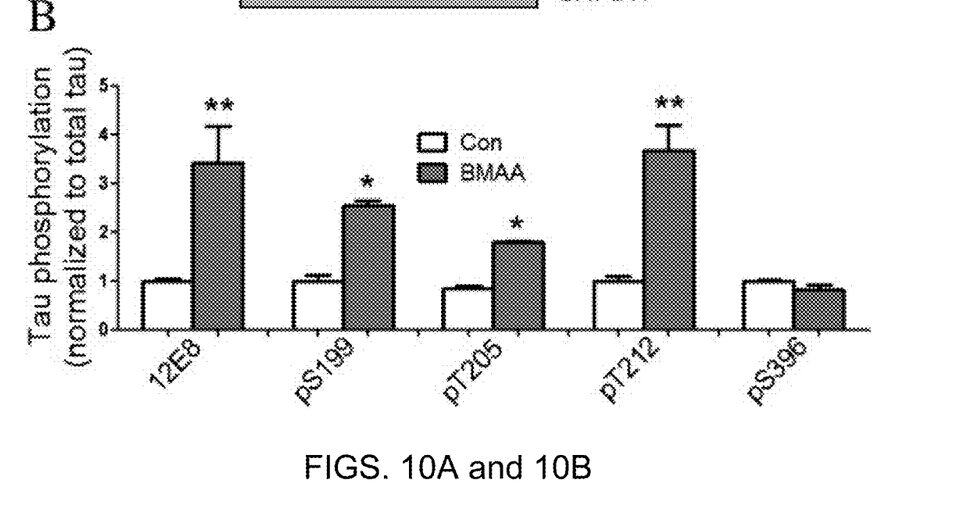

To investigate (i) whether BMAA has an effect on tau hyperphosphorylation in brain similar to that seen in primary neuronal cultures and (ii) whether the PP2A signaling involved in this effect is similar to that found in PD brains, metabolically active brain slices from adult Wistar rats were treated with 1 mM BMAA for 2-3 h. The level of tau phosphorylation was determined, the involvement of PP2A and tau kinases regulated by it was studied. BMAA increased phosphorylation of tau at $Ser^{262/356}$ (3.4-fold), $Ser^{199}$ (2.6-fold), $Thr^{205}$ (1.8-fold), and $Thr^{212}$ (3.7-fold), as seen in FIGS. 10A and 10B. As in primary hippocampal neurons, there was not any significant change in the phosphorylation of tau at $Ser^{396}$, as seen in FIG. 10B. Next, PP2A activity was assayed and a significant inhibition of PP2A activity in brain slices incubated with BMAA for 2 h in artificial cerebrospinal fluid was found, as seen in FIG. 3A. To understand the mechanism underlying BMAA-induced down-regulation of PP2A, phosphorylation of PP2A at $Tyr^{307}$, demethylation at $Leu^{309}$, and the levels of the PP2A inhibitors $I_1^{PP2A}$ and $I_2^{PP2A}$ were measured. A dramatic (3.7-fold) increase was found in the phosphorylation of PP2Ac at $Tyr^{307}$ in BMAA-treated slices, but no significant changes were detected in the level of $Leu^{309}$ demethylated PP2A, $I_1^{PP2A}$, or $I_2^{PP2A}$, as seen in FIGS. 3B and 3C.

Figure 3D:
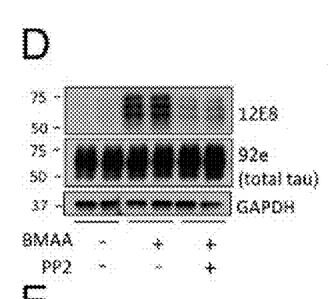
Figure 3E:
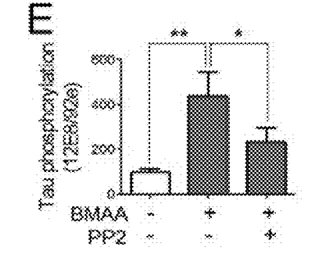

It is known that Src family kinases such as c-Src and Lck phosphorylate PP2Ac at $Tyr^{307}$ and inhibit its activity. It was thus examined whether Src could play a role in BMAA-induced PP2A inactivation. Pretreatment with PP2, a broad-spectrum Src kinase inhibitor, blocked the BMAA-induced tau hyperphosphorylation in brain slices, as seen in FIGS. 3D and 3E.

Figures 3F, 3G:
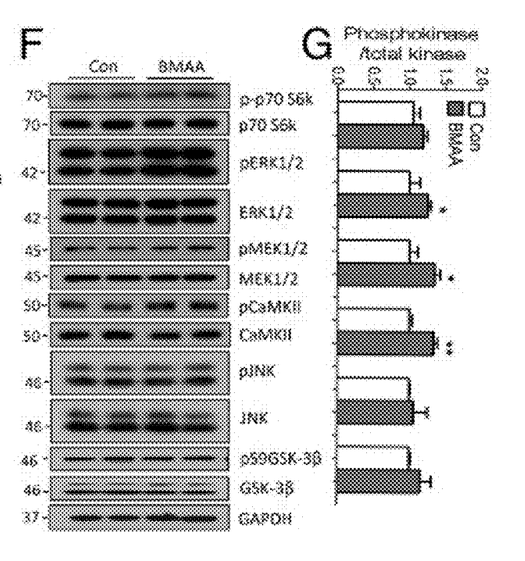
Figure 11A:
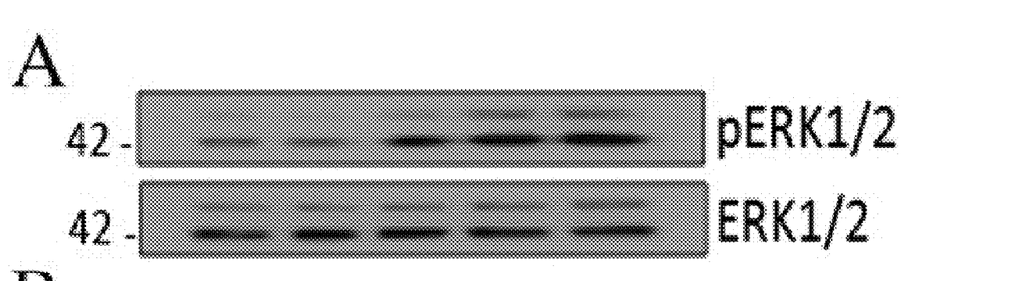
FIGS. 11A and 11B are images showing the inhibition of PP2A induces ERK1/2 phosphorylation. Primary neurons were treated with the PP2A inhibitor okadaic acid (OA, 10-100 nM) for 30 min and were processed for ERK1/2 analysis. (A) Representative Western blots showing phosphorylation of ERK1/2. (B) Quantitative analysis of pERK1/2 after normalization with total ERK1/2. Data are expressed as mean±SEM. *P<0.05; **P<0.01.
Figure 11B:
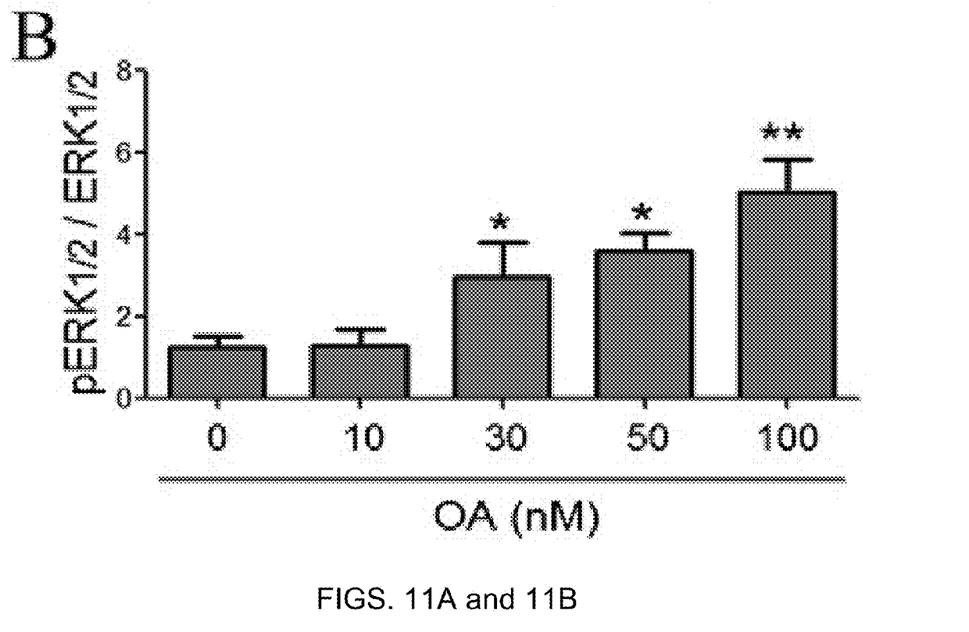

PP2A can regulate phosphorylation of tau both directly and through the activation of several tau protein kinases that are regulated by it. As a result, levels of total and activated/inactivated forms of several PP2A regulated protein kinases were measured. The levels of phosphorylated/activated CaMKII, ERK1/2, and MEK1/2 increased noticeably after treatment with BMAA, as seen in FIGS. 3F and 3G. However, no significant changes in the levels of phosphorylated GSK-3β, JNK, or p70 S6 kinase were detected in BMAA-treated brain slices. The inhibition of PP2A activity by okadaic acid up-regulates ERK1/2 phosphorylation, similar to the findings following BMAA treatment, as seen in FIG. 11. However, involvement of any nonspecific cytotoxic effect of BMAA in increasing the phosphorylation of ERK1/2 cannot be ruled out. Collectively these results suggest that (i) inhibition of PP2A plays an important role in BMAA-induced tau hyperphosphorylation, (ii) the effect of BMAA is modulated both directly by PP2A and indirectly by the tau kinases that are regulated by PP2A, and (iii) the effect of BMAA on PP2A signaling in brain slices is similar to the effect observed in PD brains.

Figures 4A, 4B, 4C, 4D:
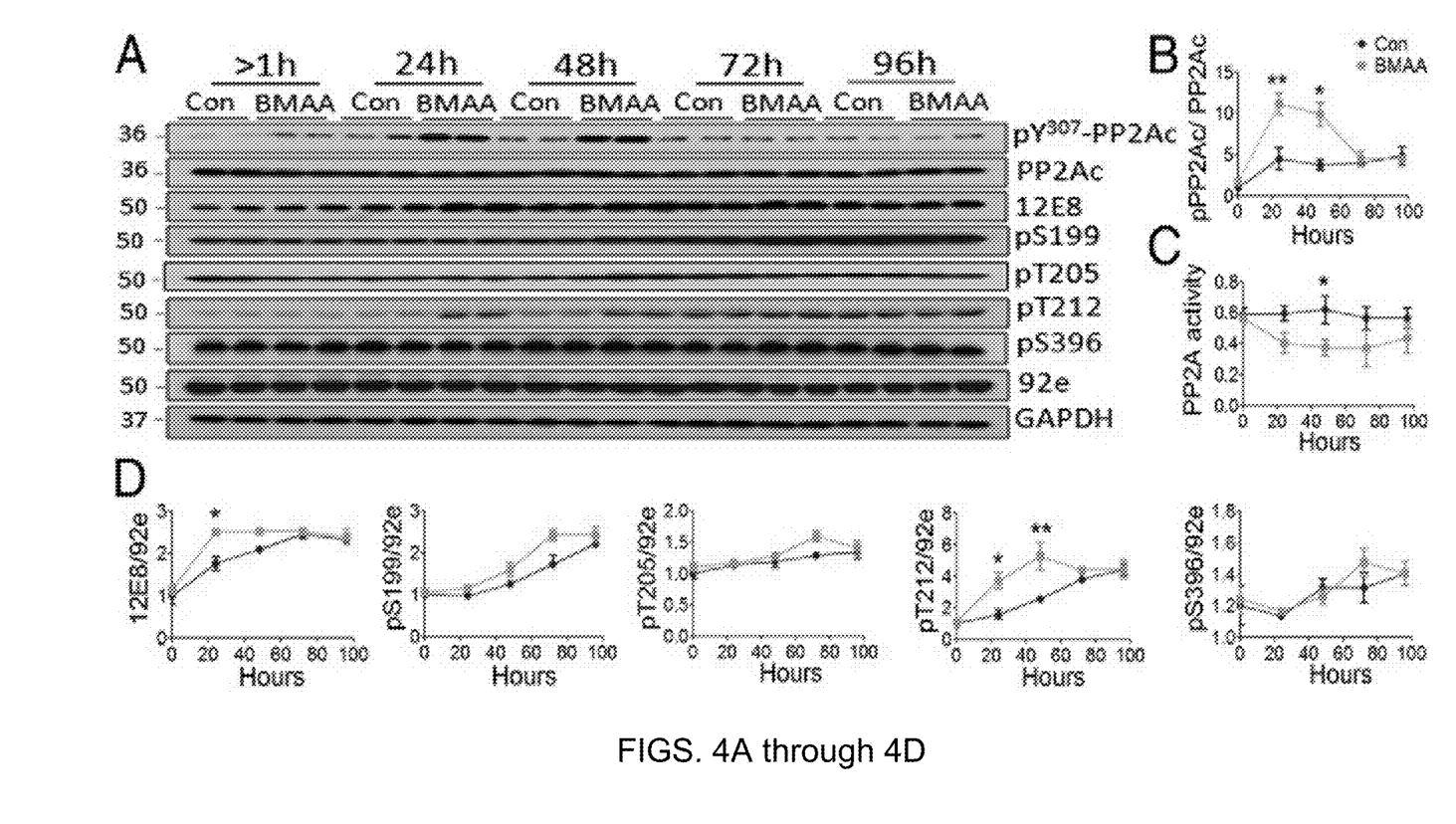
FIG. 4A through 4D are a series of charts and images showing that the i.c.v. infusion of BMAA induces an increase in $pTyr^{307}$-PP2Ac, inhibition of PP2A activity, and hyperphosphorylation of tau in vivo in rat pups. Rat postnatal day 2 hippocampus was collected at the indicated time points after i.c.v. injection of BMAA (1.3 μmol) and was analyzed by Western blots to detect tau phosphorylation at individual sites and PP2A phosphorylation at $Tyr^{307}$. (A) Representative Western blots. (B) $pTyr^{307}$-PP2A level normalized with total PP2A level. (C and D) PP2A activity (C) and quantification of hyperphosphorylation of tau normalized with total tau (92e) (D). Data are expressed as mean±SEM for two separate experiments (n=4-5). pPP2Ac, $pY^{307}$-PP2Ac. *P<0.05; **P<0.01.

The effect of BMAA on tau hyperphosphorylation in vivo in rat brain was also studied. Because of poor blood-brain barrier permeability of BMAA in the adult as compared with the neonatal brain, newborn rats were selected for these studies. BMAA was administered intracerebroventricularly (i.c.v.) in neonatal rats and then at various time points analyzed their brains for changes in PP2A and hyperphosphorylation of tau. After BMAA treatment, the level of phosphorylation of PP2Ac at $Tyr^{307}$ in rat brains increased markedly for 24-48 h and then decreased to a normal level by 72-96 h, as seen in FIGS. 4A and 4B. Correspondingly, PP2A activity decreased, and this change was most significant at 48 h after BMAA treatment, as seen in FIG. 4C. In BMAA-treated rats the hyperphosphorylation of tau at $Ser^{262/356}$ and $Thr^{212}$ peaked at 24-48 h, whereas phosphorylation at $Ser^{199}$, $Thr^{205}$, and $Ser^{396}$ peaked at 72-96 h, as seen in FIG. 4D; in vehicle-treated rats the hyperphosphorylation of tau at all the sites studied also reached the highest levels by 72-96 h. Together these findings revealed that the effect of BMAA on PP2A signaling in vivo in rat brain was similar to the changes in PP2A observed in PD brains and that hyperphosphorylation of tau at $Ser^{262/356}$ and $Thr^{212}$ precedes that at $Ser^{199}$, $Thr^{205}$, and $Ser^{396}$ in BMAA treated rats.

Figure 5A:
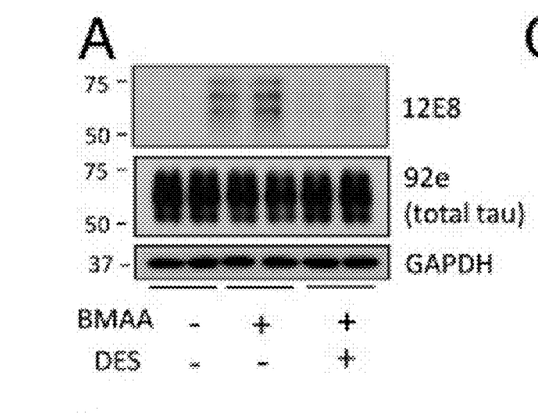
FIGS. 5A through 5E are a series of charts and images showing that up-regulation of PP2A by DES or PP2A (DsRed) reverses BMAA-induced tau hyperphosphorylation in rat brain slices and mouse hippocampal primary neurons as follows: (A) Western blots of brain slices treated with BMAA (1 mM) for 2 h with or without pretreatment with the PP2A activator DES (15 nM). (B) Quantitation of the blots in A. (C) The primary hippocampal neurons were transfected with DsRed-vector or DsRed-PP2Ac at 6 days in vitro (DIV) and then were treated with BMAA (1 mM) for 3 h at 8 DIV. The neurons were fixed and costained with DsRed (red) and 12E8 (green). (Scale bar, 50 μm.) (Magnification: 40×). (D) Quantitation of 12E8 staining normalized with DsRed. (E)
Figure 5B:
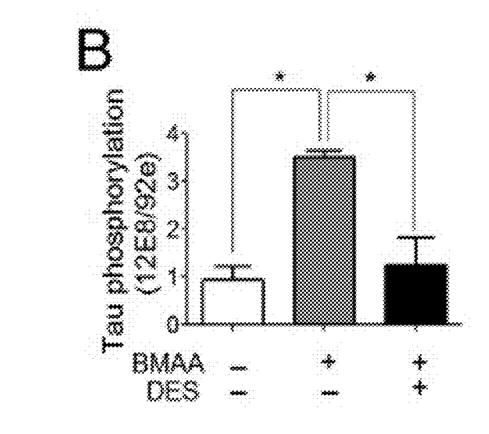
Figure 5C:
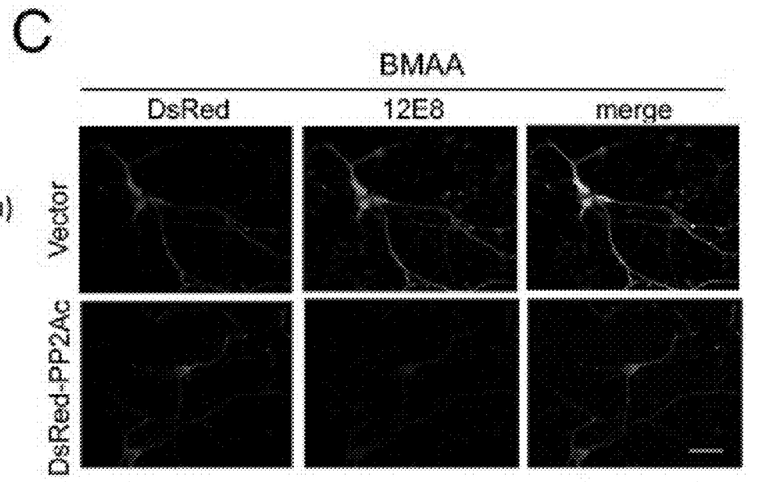
Figure 5D:
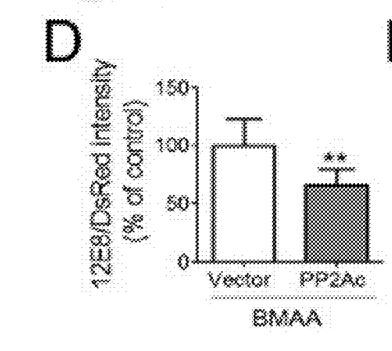
Figure 12:
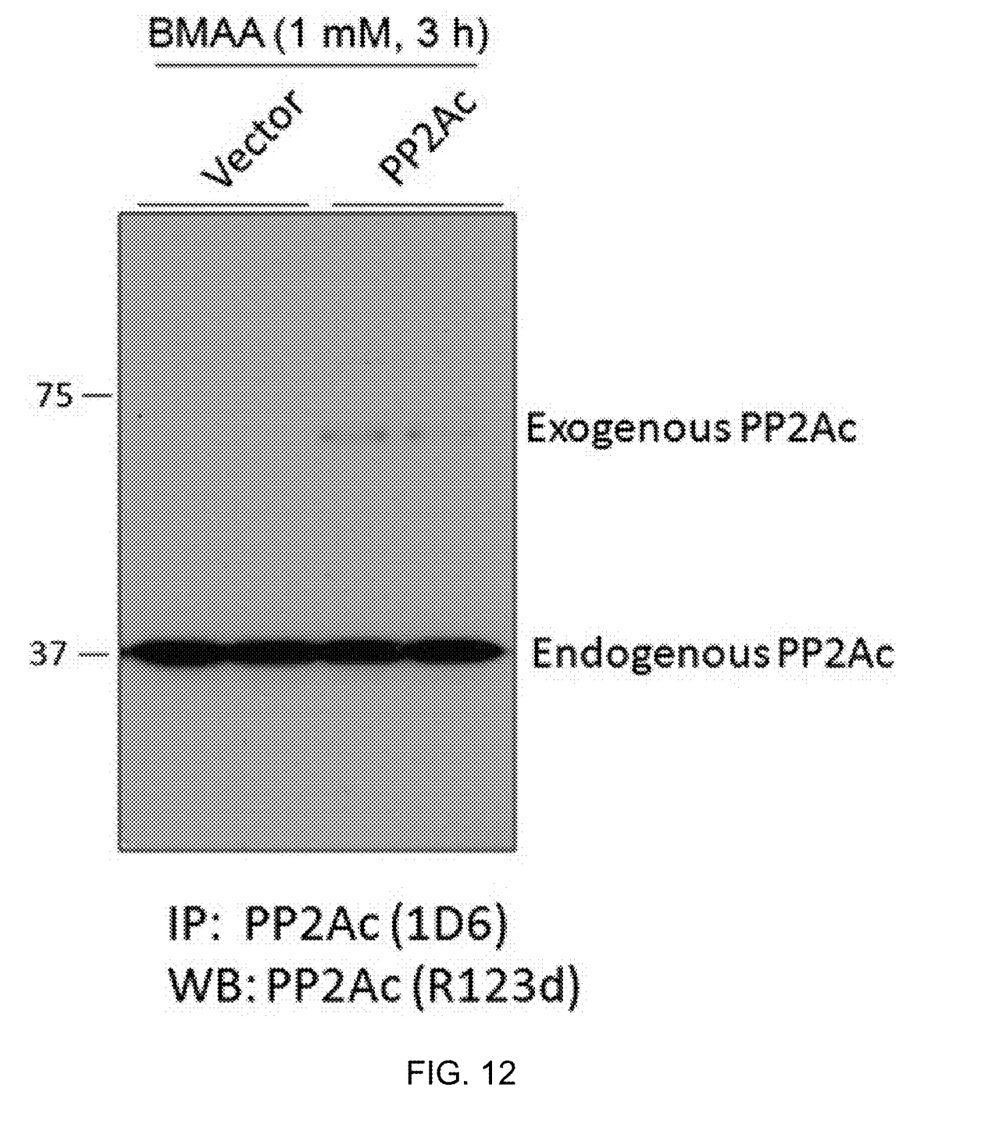
FIG. 12 is an image of the exogenous expression of PP2Ac in neurons. Primary neurons were transfected with vector (DsRed) or DsRed-PP2Ac and then were treated with BMAA. The cell lysate was used for immunoprecipitation with anti-PP2Ac antibody. The expression of exogenous PP2Ac was determined by Western blots. Representative Western blots show the presence of expressed DsRed-PP2Ac in neurons as a 67-kDa fusion protein.

To confirm the role of PP2A in BMAA-induced tau hyperphosphorylation, metabolically active rat brain slices were treated with D-Erythro-S (DES), a PP2A activator, or expressed wild-type DsRed-tagged PP2Ac in primary neurons before BMAA treatment. Either activation of PP2A, as seen in FIGS. 5A and 5B, or overexpression of PP2Ac, as seen in FIGS. 5C and 5D and FIG. 12, blocked the BMAA-induced tau hyperphosphorylation.

Figure 5E:
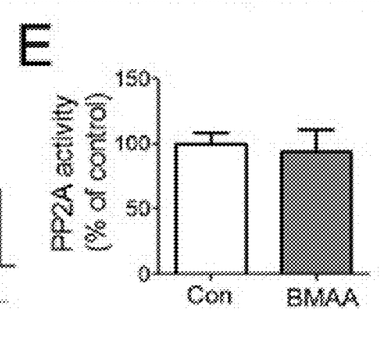

To evaluate whether BMAA has any direct effect on PP2A, an in vitro PP2A activity assay was performed using bovine purified PP2A holoenzyme in the presence or absence of BMAA, as seen in FIG. 5E. No effect of BMAA on PP2A activity was found. Collectively, these findings suggest that BMAA does not promote PP2A inactivation directly but most probably affects its signaling.

Figure 6A:
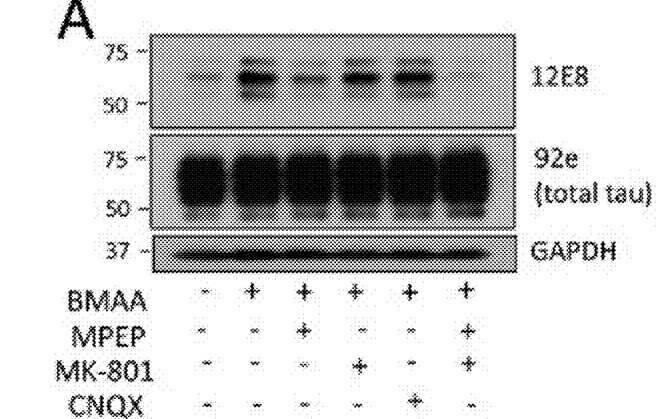
FIGS. 6A through 6E are a series of charts and images showing that BMAA induces tau hyperphosphorylation by activating mGluR5. Rat Hippocampal brain slices were incubated with BMAA (1 mM) for 2 h with or without the 30-min pretreatment with MPEP (50 μM), MK-801 (10 μM), or CNQX (20 μM) as follows: (A) Representative Western blots. (B) Quantitation of blots from A. (C) PP2A activity. (D) PP2Ac immunoprecipitates blotted for coimmunoprecipitating mGluR5 after BMAA treatment in primary neuronal cultures. (E) Quantitation of data from D. Data are expressed as mean±SEM for three separate experiments. *P<0.05; **P<0.01.
Figure 6B:
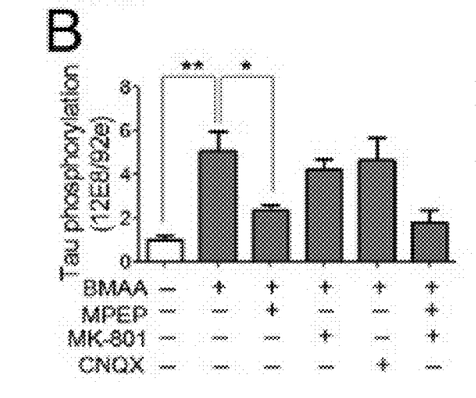
Figure 6C:
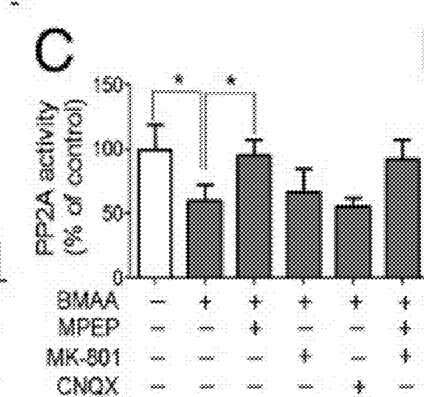

To identify the up-stream molecular mechanism involved in BMAA-induced PP2A ($Tyr^{307}$) phosphorylation, rat brain slices were incubated with and without 2-methyl-6-(phenylethynyl)pyridine (MPEP, an antagonist of mGluR5), MK-801 (an antagonist of NMDA), or 6-cyano-7-nitroquinoxaline-2,3-dione (CNQX, an antagonist of AMPA) for 30 min before the addition of BMAA. The preincubation of the brain slices with 50 µM MPEP significantly blocked tau hyperphosphorylation at the 12E8 site induced by BMAA, but no significant change was observed when the slices were treated with either MK-801 (10 µM) or CNQX (20 µM) alone, as seen in FIGS. 6A and 6B. The BMAA induced decrease in PP2A activity was blocked completely by pretreatment with MPEP but not with MK-801 or CNQX, as seen in FIG. 6C. Interestingly, cotreatment with MPEP and MK-801 entirely prevented the BMAA-induced tau hyperphosphorylation and PP2A inhibition. These data suggest that the activation of the mGluR5 receptor might be primarily involved in the inactivation of PP2A and the resultant hyperphosphorylation of tau in BMAA-treated brain slices.

Figure 6D:
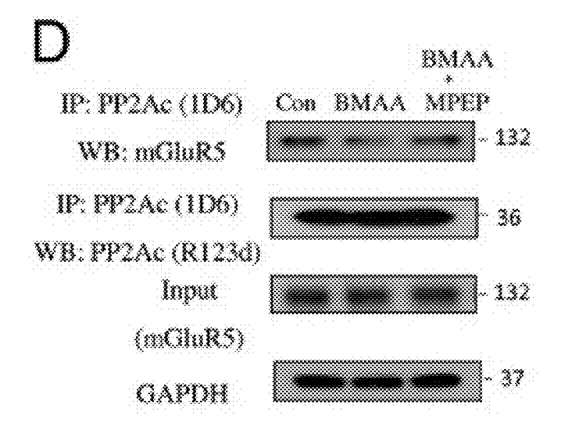
Figure 6E:
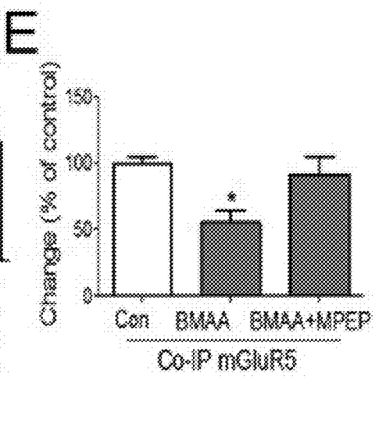

PP2A is known to be associated with mGluR5, and activation of mGluR5 leads to the dissociation of PP2A from this receptor and consequently to PP2A inactivation. To confirm whether mGluR5 activation is the underlying cause of PP2A inactivation through dissociation, coimmunoprecipitation experiments were carried out and the amount of PP2Ac associated with mGluR5 in primary neurons in the presence or absence of 1 mM BMAA was analyzed. The treatment of the primary neuronal cultures with BMAA led to the dissociation of PP2Ac from mGluR5, and cotreatment with MPEP completely blocked the dissociation of PP2A from the receptor, as seen in FIGS. 6D and 6E. These data suggest that BMAA induced mGluR5 activation probably leads to the dissociation and consequently to the inactivation of PP2A by its phosphorylation at $Tyr^{307}$.

Neurofibrillary pathology made up of abnormally hyperphosphorylated tau is a hallmark of several neurodegenerative diseases which, in addition to PD, include AD, frontotemporal dementia-tau, Pick disease, cortico-basal degeneration, progressive supranuclear palsy, and adults with Down syndrome, suggesting that several different etiopathogenic mechanisms probably lead to this lesion. Thus, elucidation of these various mechanisms is critical for the development of rational therapeutic drugs for these diseases and is a major goal in the field. Off and on, over the last five decades, BMAA has been considered a candidate neurotoxin in Guam ALS and PD, but experimental evidence to support its role has been lacking. The present invention identifies the association of tau pathology with a decrease in PP2A activity and increased phosphorylation of PP2Ac at $Tyr^{307}$ as a cause of this deficit in the phosphatase activity in PD. Furthermore, all the changes in PD brains can be replicated by treatment with BMAA in rat brain.

Figure 7:
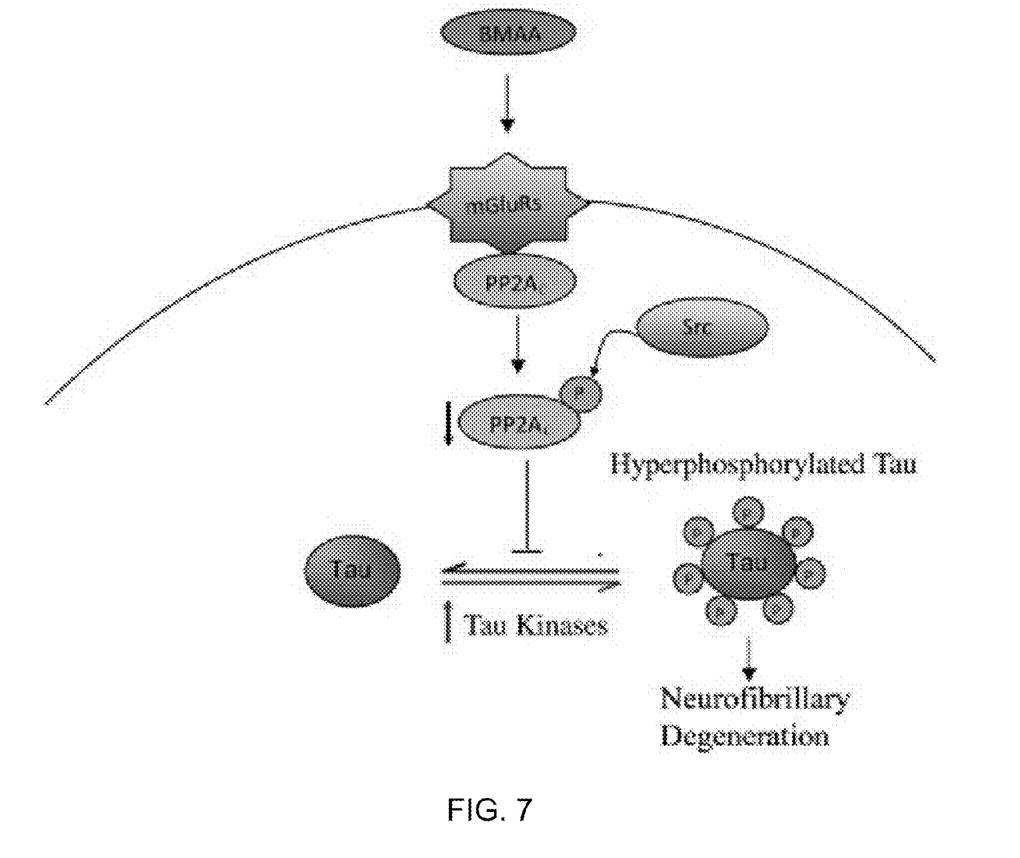
FIG. 7 is schematic representation of the possible mechanism leading to neurofibrillary degeneration in PD. BMAA activates the mGluR5 receptor and dissociates PP2Ac from the receptor. Src kinase then acts on free and available PP2Ac and phosphorylates at $Tyr^{307}$, inhibiting its activity and shifting the balance toward tau kinases, thus leading to the hyperphosphorylation of tau as evident in Guam PD brain.
Figure 8A:
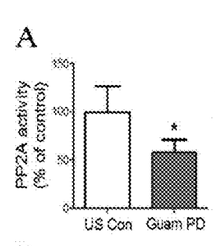
FIGS. 8A through 8E are a series of graphs showing phosphorylation of PP2Ac at $Tyr^{307}$ results in inhibition of PP2A and hyperphosphorylation of tau in Guam PD brain. (A) Brain homogenate from Guam PD frontal cortices and nonneurological control frontal cortices from the United States mainland was used to assay PP2A activity using ELISA. (B) Western blots of PP2A and its inhibitors. (C) Quantitative analysis of blots in B. (D) Quantitative Western blots developed with phospho-dependent tau antibodies. (E) Quantitative analysis of blots in D. Data are expressed as mean±SEM. *P<0.05; P<0.01; *P<0.001.
Figure 8B:
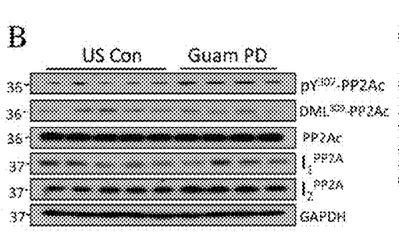
Figure 8C:
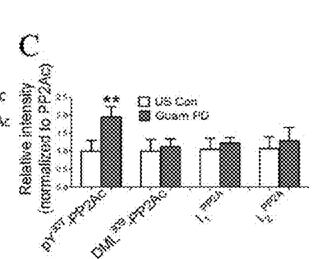
Figures 8D, 8E:
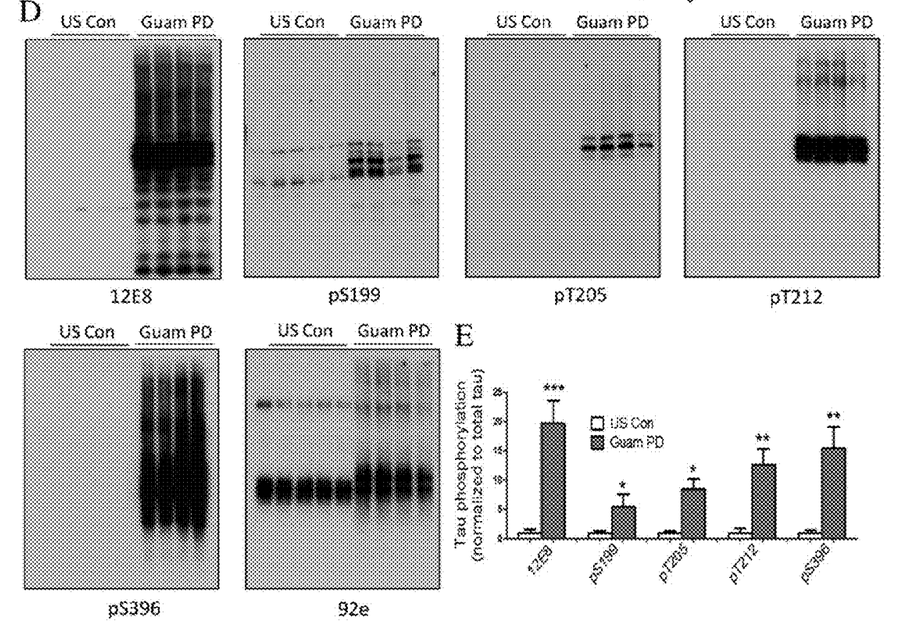
Figure 9A:
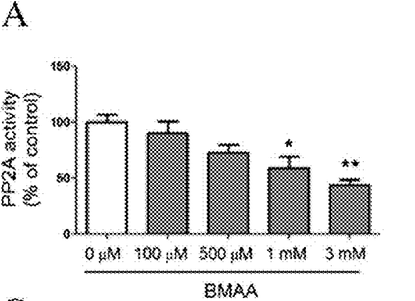
FIGS. 9A through 9D are a series of graphs showing dose-dependent effect of BMAA on PP2A activity. (sl) PP2A activity in primary hippocampal neurons was assayed 3 h after treatment with 100 μM to 3 mM BMAA. (B) Western blot pattern of PP2Ac and quantified data. (C) Time course of PP2A activity after treatment with 30 μM to 500 μM of BMAA for 0, 3, 24, or 48 h. (D) PP2Ac Western blots (Upper) and quantitation of blots (Lower). Data are expressed as mean±SEM for two separate experiments. *P<0.05; **P<0.01.
Figure 9B:
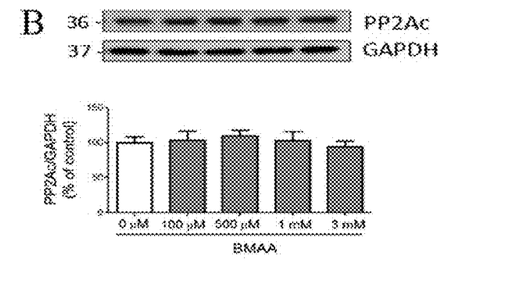
Figure 9C:
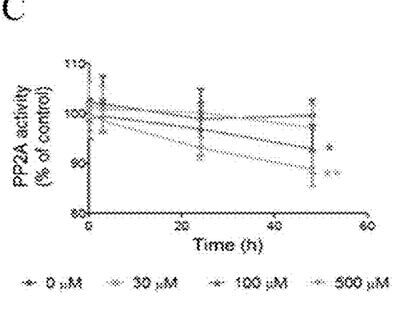
Figure 9D:
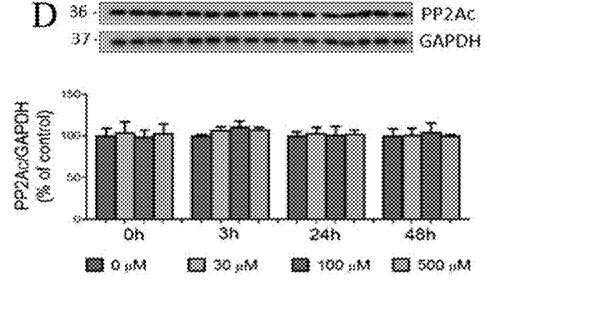

Treatment with BMAA: (i) can produce an increase in phospho$Tyr^{307}$-PP2Ac, (ii) can inhibit PP2A activity, and (iii) can produce abnormal hyperphosphorylation of tau in hippocampal primary neurons, in metabolically active brain slices, and in vivo in rats. Finally, using primary neurons and brain slices, BMAA produces the increase in phospho-$Tyr^{307}$-PP2Ac and consequent hyperphosphorylation of tau by activating mGluR5, leading to the dissociation of PP2Ac from the receptor and then its phosphorylation at $Tyr^{307}$ by Src. Although Src activity was not measured, the report that Src activity is up-regulated mainly through $Tyr^{416}$ phosphorylation certainly rules out the direct possible involvement of BMAA, because it is not a kinase. This molecular mechanism, as seen in FIG. 7, is different from that involving cerebral ischemia and hypoxia, which inhibit PP2A by the activation of asparaginyl endopeptidase and the consequent cleavage and translocation of $I_2^{PP2A}$ in AD and ALS.

BMAA exposure is not localized to Guam but rather is ubiquitous throughout the world. BMAA can enter the food chain from cyanobacteria, can be incorporated into plant and animal proteins, and can be bio-concentrated in the ecosystem.

The bound form of BMAA may function as an endogenous neurotoxic reservoir, releasing free BMAA and causing neurodegeneration. BMAA promotes neuronal death both in vitro and in vivo. In the present invention, 1 mM BMAA caused cell death in mixed primary neuronal cultures. 1 mM BMAA was used for most of the experiments, considering that the reported average brain concentrations of the compound in Guam PD and North American AD cases were 627 µg/g, 5 mM and 95 µg/g, 0.8 mM, respectively. Therefore, the 1 mM BMAA concentration used for modeling PD-related pathology is highly relevant.

In the AD brain phospho-Tyr$^{307}$-PP2Ac is increased, and phosphatase activity is decreased. Thus, taken together, tau phosphorylation may result from an environmental as well as from an endogenous toxin, such as BMAA, and this mechanism could be common to AD, PD, and ALS.

The inhibition of PP2A activity could be accounted for by the phosphorylation of PP2Ac at Tyr$^{307}$. Similar results were observed in the rat brain slices and in vivo in rat brain by treatment with BMAA. Pre-incubation of brain slices with PP2, an inhibitor of Src responsible for PP2A (Tyr$^{307}$) phosphorylation, significantly attenuated BMAA-induced tau phosphorylation, suggesting that BMAA may inhibit PP2A through Tyr$^{307}$ phosphorylation. The critical role of PP2A in BMAA-induced tau hyperphosphorylation was confirmed further by both pharmacological and genetic approaches; the activation of PP2A by DES in brain slices and the overexpression of PP2Ac in primary neuronal cultures entirely prevented the hyperphosphorylation of tau when treated with BMAA. The increase observed in the activation of CaMKII, ERK1/2, and MEK1/2 by BMAA in rat brain slices probably is secondary to the inhibition of PP2A, which is known to regulate these kinases.

A marked increase was found in the abnormal hyperphosphorylation of tau in PD brains at Ser$^{199}$, Thr$^{205}$, Thr$^{212}$, and Ser$^{262/356}$. All these phosphorylation sites are known to be involved in promoting the assembly of tau into filaments. Similar patterns of hyperphosphorylation of tau in BMAA-treated primary neurons and brain slices were observed. Among all the sites investigated, Ser$^{262}$ and Ser$^{356}$ reside within the microtubule-binding domains of tau, and phosphorylation of Ser$^{262}$ is most implicated in inhibition of tau's interaction with microtubules. Although Ser$^{199}$, Thr$^{205}$, and Thr$^{212}$ are not within the microtubule-binding domains, the phosphorylation of these sites primes the phosphorylation at other sites as well as increasing tau's microtubule inhibitory activity and self-aggregation into filaments. In addition to the phosphorylation of tau at different sites, some interesting time-dependent sequential changes of tau site-specific phosphorylation in BMAA-infused neonatal rat brain were observed. Phosphorylation of Ser$^{262/356}$ and Thr$^{212}$ preceded the appearance of phosphorylation at Ser$^{199}$ and Thr$^{205}$. The earlier phosphorylation of Ser$^{262}$ is in agreement with the observation that this phosphorylation detaches tau from microtubules and thereby makes it available for the formation of PHFs.

In line with these findings, it has been reported that the pre-neurofibrillary tangles stain positively primarily for pSer$^{262/356}$, whereas both intra- and extracellular NFTs stain positively most prominent for pSer$^{199}$/pSer$^{202}$/pThr$^{205}$, pThr$^{212}$/pSer$^{214}$, and pSer$^{396}$/pSer$^{404}$. In contrast it was observed that pSer$^{396}$ expression was unchanged in BMAA treated mouse hippocampal primary neuronal cultures, hippocampal brain slices, and even in in vivo rat brain. The apparent discrepancies may be caused by the genomic and cellular complexity of human vs. mouse/rat tissues. Another possible explanation could be that Ser$^{396}$ is the least favorable site for dephosphorylation by PP2A in response to BMAA treatment. Based on the data in the present study, it is reasonable to delineate an association between disease progression and abnormal hyperphosphorylation of tau at specific sites in PD, similar to those reported previously in AD.

The present invention suggests the direct involvement of a PP2A dependent disease mechanism. PP2A has been shown to form a complex with NMDA and mGluR5 receptors, and dissociation of PP2A from these receptors reduces PP2A activity. Moreover, BMAA has been reported to affect all the main glutamate receptors, i.e., NMDA, AMPA/kainate, and metabotropic receptors. This evidence suggests that the effect of BMAA on either NMDA or mGluR5 can facilitate PP2A inactivation through dissociation from the receptor. In the present invention, however, it was found that activation of mGluR5, but not of the NMDA receptor, was responsible for BMAA-induced tau hyperphosphorylation in brain slices. In the present invention, coimmunoprecipitation experiments further confirmed that the activation of mGluR5 dissociates PP2A from the mGluR5 receptor. Taken together, the results of the present study suggest that activation of mGluR5 facilitates a series of biochemical events, including dissociation of PP2A from mGluR5, Tyr$^{307}$ phosphorylation of PP2Ac, reduction of PP2A activity, and tau hyperphosphorylation. Based on these findings, the involvement of a mechanistic pathway may underly the neurofibrillary degeneration in PD, so that an environmental toxin, such as BMAA, down-regulates PP2A activity and induces tau hyperphosphorylation by activating mGluR5; the activation of mGluR5 results in the dissociation of PP2Ac from the receptor, followed by its phosphorylation at Tyr$^{307}$ by Src.

Example

Human Brain Tissue

Frozen autopsied tissue samples of frontal cortices from Guam nonneurological controls (n=7) and Guam parkinsonism-dementia (PD) (n=8 used in FIG. 1 and n=4 used in FIG. 8) cases were obtained from Ralph M. Garruto, National Institute of Neurological Disorders and Stroke, National Institutes of Health and the Biospecimen Archive Facility, State University of New York, Binghamton. The nonneurological control cases from the United States mainland (n=5) were from Sun Health Research Institute Brain Donation Program (Sun City, Ariz.) and from the Harvard Brain Bank, McLean Hospital (Belmont, Mass.). The ages, sex, and neurofibrillary tangles (NFT) of the PD and control cases are listed in Tables 1 and 2 below.

TABLE 1

First set of Guam PD and Guam nonneurological control cases from which the brain tissues were used in this example.

| Case | Age at onset, y | Age at death, y | Sex | NFT |
| --- | --- | --- | --- | --- |
| Guam control-1 | N/A | 66 | F | Absent |
| Guam control-2 | N/A | 48 | F | Absent |
| Guam control-3 | N/A | 57 | F | Absent |
| Guam control-4 | N/A | 68 | F | Few |
| Guam control-5 | N/A | 43 | F | Absent |
| Guam control-6 | N/A | 65 | M | Absent |
| Guam control-7 | N/A | 58 | M | No pathology |
| Mean ± SD | | 57.86 ± 9.47 | | |
| Guam PD-1 | 53 | 62 | M | Severe |
| Guam PD-2 | 56 | 63 | M | Moderate |
| Guam PD-3 | 48 | 52 | F | Severe |
| Guam PD-4 | 64 | 73 | F | Severe |
| Guam PD-5 | 71 | 73 | F | Severe |
| Guam PD-6 | 42 | 53 | F | Severe |
| Guam PD-7 | 59 | 62 | M | Severe |
| Guam PD-8 | 45 | 51 | F | Severe |
| Mean ± SD | | 61.13 ± 8.77 | | |

TABLE 2

Second set of Guam PD and nonneurological control cases from the United States mainland from which the brain tissues were used in this study

| Case | Age at onset, y | Age at death, y | Sex | NFT |
|---|---|---|---|---|
| US mainland control-1 | N/A | 73 | M | Absent |
| US mainland control-2 | N/A | 78 | M | Absent |
| US mainland control-3 | N/A | 65 | F | Absent |
| US mainland control-4 | N/A | 70 | F | Absent |
| US mainland control-5 | N/A | 78 | M | Absent |
| Mean ± SD | | 72.8 ± 5.54 | | |
| Guam PD-1 | 57 | 72 | M | Severe |
| Guam PD-2 | 52 | 63 | M | Severe |
| Guam PD-3 | N/A | 64 | F | Severe |
| Guam PD-4 | N/A | 81 | F | Severe |
| Mean ± SD | | 70.0 ± 8.36 | | |

The use of frozen human brain tissue was in accordance with the US National Institutes of Health guidelines and was approved by the Institutional Review Boards of the New York State Institute for Basic Research in Developmental Disabilities and the State University of New York at Binghamton. The tissue was processed as described below (see Preparation of Rat Brain Slices and β-N-Methylamino-L-Alanine Treatment) for brain slices.

Primary Neuronal Cultures and Transfection

Mouse hippocampal neuronal cultures were prepared from d 18 embryos as previously described (1). Briefly, C57BL/6 pregnant female mice from Charles River Laboratories were killed by cervical dislocation. All studies were performed in accordance with the recommendations in the Guide for the Care and Use of Laboratory Animals of the National Institutes of Health (2). The protocol was approved by Institutional Animal Care and Use Committee of the New York Institute for Basic Research in Developmental Disabilities. All surgeries were performed under anesthesia, and all efforts were made to minimize suffering. Embryos were removed and placed in cold Hibernate A (BrainBits, LLC), and all the following steps were performed in ice-cold Hibernate A, under a stereoscopic (dissection) microscope placed in a laminar flow hood. Fetal brains were removed carefully, and forebrains were separated. The hippocampus, including the cortex surrounding the area of the hippocampus, was dissected and cut into small pieces using microsurgical scissors. The cut tissue was transferred with number 5 forceps to 15-mL tubes containing 0.1% trypsin in Versene (Invitrogen Life Technologies) and was incubated for 15 min at 37° C. followed by inactivation with 10% (vol/vol) FBS in Neurobasal complete medium (Neurobasal Medium supplemented with 2×B-27, 0.30% glutamine, 10% FBS, and penicillin/streptomycin, 0.1 mg/mL and 0.1 U/mL respectively). After 3 d, the cells were grown with Neurobasal medium supplemented with only 2×B-27. This procedure typically yields cultures that contain 70-75% neurons and 30-35% supporting cells (3). The cultures were maintained at 37° C. in a humidified atmosphere containing 5% $CO_2$ for 8 or 9 d before experimentation. Every 72 h, the medium was replaced with fresh medium. All medium components were purchased from Invitrogen. The neuronal transfection was performed using Lipofectamine LTX and Plus reagent at 5 d in vitro according to the manufacturer's instructions (Invitrogen). The cells were processed for immunofluorescent staining 3 d after transfection.

Preparation of Rat Brain Slices and β-N-Methylamino-L-Alanine Treatment

Male Wistar rats (Charles River Laboratories), 2-3 months old, were anesthetized by i.p. injection with 50 mg/kg Nembutal. The animals were decapitated when deeply anesthetized. The brains were removed immediately and cooled in ice-cold (4° C.) oxygenated artificial cerebrospinal fluid (aCSF) consisting of 126 mM NaCl, 3.5 mM KCl, 1.2 mM NaH2PO4, 1.3 mM MgCl2, 2 mM CaCl2, 11 mM D(+) glucose, and 25 mM NaHCO3 (pH 7.4) for 7-8 min. Each brain then was divided sagittally, and 400-μm-thick coronal slices were made with a Camden Vibraslicer (WP, Inc.). The slices were transferred into a chamber containing the oxygenated aCSF and were incubated at 33° C. for 2 h in the presence or absence of 1 mM, β-N¬methylamino-L-alanine (BMAA) dissolved in 10 mM NaHCO3 (Sigma). The oxygenation of the aCSF was carried out by bubbling the solution with a mixture of 95% O2 and 5% CO2 during the entire procedure. At the end of incubation, the brain slices were homogenized with homogenizing buffer [50 mM Tris·HCl (pH 7.4), 8.5% (wt/vol) sucrose, 2 mM EDTA, 2 mM EGTA, 10 mM (3-mercaptoethanol, 5 mM benzamidine, 0.5 mM 4-(2-Aminoethyl) benzenesulfonyl fluoride hydrochloride (AEBSF), 4 μg/mL pepstatin A, and 10 μg/mL each of aprotinin and leupepin] at a ratio of 9.0 mL buffer/1.0 g tissue slices. The homogenates were divided into two parts. One part was centrifuged at 16,000×g for 10 min, and the resulting supernatant was used to assay protein phosphatase 2A (PP2A) activity. Into the other half, an equal volume of phosphatase-inhibitor mixture (20 mM 3-glycerophosphate, 2 mM Na3VO4, and 100 mM NaF) was added immediately, and the samples were used for Western blots.

Intracerebroventricular Infusion

Wistar rats were bred and maintained under standard environmental conditions (12-h light/dark cycles, 22° C.) and were allowed free access to food and water. The animal experiments were carried out in strict compliance with protocols approved by the Animal Welfare Committee of New York State Institute for Basic Research in Developmental Disabilities. On postnatal d 2 (PND2), pups were individually cryo-anesthetized on ice, and 2 μL of 1.3 μmol BMAA in PBS was injected into lateral ventricle using a 10-μL Hamilton syringe (Hamilton Syringe Co.). Control animals were injected with PBS in an identical manner. After infusion of BMAA, rats were killed within 1, 24, 48, 72, or 96 h, and the brains were used for Western blots and PP2A activity assays.

Coimmunoprecipitation

Mouse hippocampal cell proteins were prepared with low-stringency lysis buffer [50 mM Hepes (pH 7.4), 10% (vol/vol) glycerol, 1.5 mM $MgCl_2$, 5 mM NaF, 1 mM $Na_3VO_4$, 1 mM EDTA, 1 mM EGTA, 1% Nonidet P-40, 5 mM AEBSF, 10 μg/mL aprotinin, leupeptin, pepstatin] and were homogenized by several freeze-thaw cycles followed by water bath sonication. The homogenate was centrifuged at 14,000×g at 4° C. for 15 min. For transfection experiments with vector (DsRed) and with DsRed-PP2A catalytic subunit (PP2Ac), primary neurons were processed in a similar manner. The supernatants then were used for immunoprecipitation with mouse anti-PP2A (1D6; Millipore) followed by incubation with protein G-Sepharose (Thermo Scientific). The Western blots of immunoprecipitates were probed with rabbit anti-mGluR5 (Millipore) and rabbit anti-PP2Ac [R123d] (FIG. 55).

PP2A Activity

PP2A activity was assayed with homogenate of rat brain slices using the phosphatase ELISA described previously (5). Briefly, 96-well plates were precoated with a 17-aa phosphopeptide corresponding to tau amino acids 194-207 in which $Ser^{309}$ was replaced with phosphoserine and to which KKK were added at the C terminus (coating buffer, 35 mM NaHCO3). After overnight blocking with a protein-free blocking solution (Pierce), the enzymatic reaction was performed by adding 2 µg of cell lysate protein in 60 µL of reaction buffer [50 mM TrisHCl (pH 7.0), 2 mM MnCl2, 0.1 mg/mL BSA, 20 mM (β-mercaptoethanol] at 30° C. for 30 min (in the presence or absence of 15 nM of okadaic acid) in a moist chamber. The reaction was stopped by adding 150 µL of Pierce blocking solution containing 50 mM NaF, followed by an overnight incubation with monoclonal antibody Tau-1, which recognizes tau unphosphorylated at $Ser^{198}$, $Ser^{199}$, and $Ser^{202}$. HRP-conjugated secondary antibody treatment was for 60 min at room temperature. Finally 75 µL of 3,3',5,5'-Tetramethylbenzidine substrate reagent (Sigma) was added, and the colorimetric development was measured using a microtiter plate reader at a wavelength of 650 nm.

SDS/PAGE, Western Blots, and Quantification by Densitometry

Protein was fractionated by 10% SDS/PAGE, transferred to PVDF membrane, and then blocked with 5% skim milk for 1 h at room temperature. The membrane was probed with anti-IPP2A (5G6, 1:1, 500) (7), anti-I2P2A (10E7, 1:1, 600) (7), anti-tau ~92e; 1:5,000) (8), anti-tau (R134d; 1:5 000) (9), anti-tau $pSer^{262}/^{356}$ (12E8; 1:500) (10, anti-tau $pSer^{199}$, anti-tau $pThr^{205}$, anti-tau $pThr^{212}$, and $pSer^{396}$ (1:1,000) (Biosource), anti-GAPDH (1:2,000) (Santa Cruz Biotechnology), anti-PP2Ac (1:10 000) (BD Transduction Lab), anti $pY^{307}$-PP2A and anti-$DML^{309}$-PP2A (1:1,000) (Millipore), anti-GSK-3(α/β), anti-$pS^9$-GSK-3 β, anti-ERK1/2, anti-$pT^{202}/Y^{204}$-ERK1/2, anti-MEK1/2, anti-$p9^{17/221}$-MEK1/2, anti-CAMKII, anti-$pT^{286}$-CAMKII, anti-p70 S6 kinase, anti-$pT^{389}$-p70 S6 kinase, anti-SAPK/JNK, and anti-$pT^{183}/Y^{185}$-SAPK/JNK (1:1,000) (Cell Signaling Technology). The membrane then was incubated with HRP-conjugated secondary antibody (Jackson ImmunoResearch). The protein bands were detected with the enhanced chemiluminescence reagents (Thermo Scientific). Band intensity was measured by Multi-Gauge V3 software (Fuji Photo Film).

Immunofluorescent Staining

Primary hippocampal neuronal cultures grown on four-chamber glass slides were fixed in cold 4% (wt/vol) paraformaldehyde for 15 min and permeabilized in 0.1% Triton X-100 for 15 min followed by incubation in 5% goat serum to block the nonspecific staining for 1 h. The cells then were probed with 12E8 (1:200) overnight at 4° C. Alexa-488-conjugated anti-mouse secondary antibody (1:500) (Jackson Laboratory) was used for fluorescent labeling. The cells on slides were rinsed with PBS, mounted with Fluorogel (Electron Microscopy Sciences) and examined under laser confocal microscope (Nikon Eclipse 90i). For quantitative analysis, the images were captured using the 40× objective, and the antibody staining was quantified by measuring mean pixel intensity (MPI) with the software Image ProPlus 5.0 (Media Cybernetics) as described previously. Each experimental condition was calculated using an average number of five fields per well for three to four wells. For transfection experiments with primary neurons, 12E8 (green) MPI was normalized with that of DsRed (red) for 15-20 neurons per well, and a total four wells per experimental condition were used.

Statistical Analysis

All data are expressed as the mean±SEM. Differences among means were assessed by one-way ANOVA followed by Bonferroni post hoc test and Student t test. The value $P<0.05$ was considered statistically significant.

What is claimed is:

1. A method of treating Parkinsonism-dementia complex of Guam, comprising the step of administering a pharmaceutically effective amount of an mGluR5 antagonist to a subject in need thereof to minimize a tau hyperphosphorylation in a brain thereof, wherein the mGluR5 antagonist is 2-methyl-6-(phenylethynyl) pyridine.

2. The method of claim 1, wherein the mGluR5 antagonist is administered in a dosage of between 0.1 mg/kg and 10 mg/kg.

3. The method of claim 1, wherein the 2-methyl-6-(phenylethynyl) pyridine is administered orally.

4. The method of claim 1, wherein the tau hyperphosphorylation is a β-N-methylamino-L-alanine (BMAA)-induced tau hyperphosphorylation.

* * * * *